(12) United States Patent
Thong (10) Patent No.: US 7,930,025 B2
(45) Date of Patent: Apr. 19, 2011

(54) VENTRICULAR TACHYARRHYTHMIA PREDICTION AND/OR PREVENTION

(75) Inventor: Tran Thong, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 969 days.

(21) Appl. No.: 11/745,764

(22) Filed: May 8, 2007

(65) Prior Publication Data

US 2007/0288061 A1   Dec. 13, 2007

Related U.S. Application Data

(63) Continuation-in-part of application No. 11/177,450, filed on Jul. 7, 2005, now Pat. No. 7,471,982.

(51) Int. Cl.
*A61N 1/39* (2006.01)

(52) U.S. Cl. .................. 607/5; 607/17; 607/9; 600/518

(58) Field of Classification Search ........................ 607/5
See application file for complete search history.

(56) References Cited

U.S. PATENT DOCUMENTS

| | | | |
|---|---|---|---|
| 4,979,110 A | | 12/1990 | Albrecht et al. |
| 5,086,179 A | | 2/1992 | Powers et al. |
| 5,193,535 A | * | 3/1993 | Bardy et al. ..................... 607/4 |
| 5,273,049 A | * | 12/1993 | Steinhaus et al. ............. 600/508 |
| 2003/0078624 A1 | * | 4/2003 | Carlson et al. ................... 607/9 |
| 2003/0187479 A1 | * | 10/2003 | Thong ............................. 607/5 |

OTHER PUBLICATIONS

Algra et al., "Heart rate variability from 24-hour electrocardiography and the 2-year risk for sudden death," Circulation Jul. 1993, vol. 88, No. 1, pp. 180-185.

Thong et al., "Prediction of Tachyarrhythmia Episodes," Engineering in Medicine and Biology, 2002. 24th Annual Conference and the Annual Fall Meeting of the Biomedical Engineering Society, EMBS/BMES Conference, 2002. Proceedings of the Second Joint, vol. 2, pp. 1445-1446.

Thong et al., "Ventricular Tachyarrhythmia Prediction," Proceedings of the 2005 IEEE Engineering in Medicine and Biology 27th Annual Conference, Shanghai, China, Sep. 2005, pp. 3853-3856.

Burri et al., "Wavelet transform for analysis of heart rate variability preceding ventricular arrhythmias in patients with ischemic heart disease," International Journal of Cardiology, 109, 2006, pp. 101-107.

Lombardi et al., "Heart Rate Variability Patterns Before Ventricular Tachycardia Onset in Patients with an Implantable Cardioverter Defibrillator," The American Journal of Cardiology, vol. 86, Nov. 1, 2000, pp. 959-963.

Makikallio et al., "Heart Rate Dynamics Before Spontaneous Onset of Ventricular Fibrillation in Patients with Healed Myocardial Infarcts," The American Journal of Cardiology, vol. 83, Mar. 15, 1999, pp. 880-884.

Meyerfeldt et al., "Heart rate variability before the onset of ventricular tachycardia: differences between slow and fast arrhythmias," International Journal of Cardiology, 84, 2002, pp. 141-151.

(Continued)

*Primary Examiner* — Carl H. Layno
*Assistant Examiner* — Jon-Eric C. Morales
(74) *Attorney, Agent, or Firm* — Schwabe, Williamson & Wyatt (57) ABSTRACT

Embodiments of the present invention provide apparatuses and methods to predict and/or prevent episodes of ventricular tachyarrhythmia (for example, ventricular tachycardia and/or ventricular fibrillation). A method is provided for predicting an episode of ventricular tachyarrhythmia by detection and analysis of multiple patterns of vagal fatigue and/or a threshold-exceeding heart.

19 Claims, 9 Drawing Sheets

OTHER PUBLICATIONS

Pruvot et al., "Heart Rate Dynamics at the Onset of Ventricular Tachyarrhythmias as Retrieved From Implantable Cardioverter-Defibrillators in Patients with Coronary Artery Disease," Circulation, 101, May 23, 2000, pp. 2398-2404.

Reed et al., "Heart rate variability measurements and the prediction of ventricular arrhythmias," Q J Med 2005, 98, pp. 87-95.

Rubart et al., "Mechanisms of sudden cardiac death," The Journal of Clinical Investigation, vol. 115, No. 9, Sep. 2005, pp. 2305-2315.

Schmidt et al., "Heart-rate turbulence after ventricular premature beats as a predictor of mortality after acute myocardial infarction," The Lancet, vol. 353, Apr. 24, 1999, pp. 1390-1396.

Shusterman et al., "Autonomic nervous system activity and the spontaneous initiation of ventricular tachycardia," Journal of the American College of Cardiology, 1998, vol. 32, pp. 1891-1899.

Shusterman et al., "Dynamics of low-frequency R-R interval oscillations preceding spontaneous ventricular tachycardia," American Heart Journal, 2000, 139, pp. 126-133.

"Heart Rate Variability," Circulation, 1996, 93, pp. 1043-1065.

Zimmermann, "Sympathovagal Balance Prior to Onset of Repetitive Monomorphic Idiopathic Ventricular Tachycardia," PACE, vol. 28, Jan. 2005, Supplement 1, pp. S163-S167.

* cited by examiner

| Predictor | Bio-ICD database | | | | | | Surrogate-VA-ICD database | | p value: Bio-ICD vs. Surrogate-VA-ICD |
|---|---|---|---|---|---|---|---|---|---|
| | Sensitivity | | | | | Kaplan-Meier sensi-tivity (208) | False posi-tive (Kaplan-Meier) (208) | Speci-ficity (1-False posi-tive) | |
| | Devel-opment (39 records) | Other (169) | Multiple record subj. (163) | Single record subj. (45) | All (208) | | | | |
| Simple acceleration | 69% | 83% | 76% | 75% | 80% | 83% | 43% | 57% | $<10^{-4}$ |
| Simple acceleration with peak > 86 bpm | 49% | 70% | 64% | 59% | 66% | 69% | 17% | 83% | $<10^{-4}$ |
| Double acceleration | 28% | 57% | 49% | 48% | 51% | 57% | 17% | 83% | $<10^{-4}$ |
| Double acceleration with peak > 86 bpm | 21% | 53% | 42% | 46% | 47% | 53% | 9% | 91% | $<10^{-4}$ |

VENTRICULAR TACHYARRHYTHMIA PREDICTION AND/OR PREVENTION

CROSS REFERENCE TO RELATED APPLICATIONS

The present application is a continuation-in-part of and claims priority to U.S. patent application Ser. No. 11/177,450, filed Jul. 7, 2005, entitled "Ventricular Tachyarrhythmia Prediction and/or Prevention," now U.S. Pat. No. 7,471,982, the entire disclosure of which is hereby incorporated by reference in its entirety.

TECHNICAL FIELD

Embodiments of the present invention relate to life sciences and medical devices, and, in particular, to methods and apparatus for predicting and/or preventing episodes of ventricular tachyarrhythmia.

BACKGROUND

Episodes of ventricular tachyarrhythmia (VTA) are lethal arrhythmia, namely ventricular fibrillation and ventricular tachycardia, which may accelerate into ventricular fibrillation. Drug therapies may be used, but these anti-arrhythmic drugs often have undesirable side effects. Clinical experience has shown that at an acceptable level, these anti-arrhythmic drugs may reduce but not completely eliminate episodes of VTA. An effective device for treating, as opposed to preventing, VTA is the implantable cardioverter defibrillator (ICD). An ICD may be implanted in a patient at risk of sudden cardiac attack, for example, by an episode of VTA. However, an ICD may treat, but does not prevent episodes of VTA.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

DETAILED DESCRIPTION OF EMBODIMENTS OF THE INVENTION

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

For the purposes of the description, a phrase in the form "A/B" means A or B. For the purposes of the description, a phrase in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In various embodiments of the present invention, methods, apparatuses, and systems for predicting and/or preventing ventricular tachyarrhythmia (VTA) are provided. In exemplary embodiments of the present invention, a computing system may be endowed with one or more components of the disclosed apparatuses and/or systems and may be employed to perform one or more methods as disclosed herein.

Embodiments of the present invention relate to methods and apparatuses for predicting and/or preventing episodes of ventricular tachyarrhythmia and/or providing a warning of an imminent episode of VTA.

Embodiments of the present invention provide apparatuses and methods to predict an episode of ventricular tachyarrhythmia (for example, ventricular tachycardia and/or ventricular fibrillation). Embodiments of the present invention may also be used to prevent episodes of ventricular tachyarrhythmia by implementing a preventive therapy, such as a temporary pacing regimen, or other suitable procedures. Other embodiments may be used to warn the patient or a medical professional of an imminent episode of VTA.

In an embodiment of the present invention, an implantable defibrillator or similar device may be used to provide preventive therapy in response to a predictor or other indicator of an imminent episode of VTA. An imminent episode is one that may occur within a period of seconds, minutes or hours, such as less than 3 hours from a predefined predictor or indicator.

One indicator of VTA is a temporary rhythm acceleration during sinus rhythm termed a vagal fatigue pattern (VFP). This pattern is termed VFP because such a rhythm acceleration appears to be a result of a temporary depression of the parasympathetic (vagal) nervous system, but importantly simply denotes the temporary rhythm acceleration pattern regardless of the cause. Details of VFP and its use for predicting VTA may be found in U.S. Pat. No. 7,076,299, the entire contents and disclosure of which is hereby incorporated by reference. U.S. Pat. No. 7,076,299 provides details related to methods of monitoring and processing R-R intervals (or heart rate), methods of signaling or notifying a patient or medical professional of an imminent VTA, and methods of preventive action in the event an episode of VTA is predicted.

Although R-R intervals are mentioned above, in embodiments of the present invention, the heart rate, P-waves (P-P intervals), or far field measurements may be used in conjunction with or in lieu of the R-R intervals.

According to embodiments of the present invention, performance of a VFP-based VTA prediction algorithm may be measured in part by (1) using the error threshold, which may be for example 4%; (2) computing error from the reference signal, which may be an exponential average of the past R-R intervals (the fraction of the old average may be for example 95%, but may be varied from 90% to 99%); (3) calculating the number of R-R intervals with error above a threshold, such that at a value, which may be, for example 65, it may be determined that a VFP has been detected; and (4) exponentially decaying the R-R counter using, for example, 90% of the previous value, such that when the count reaches a value, which may be for example 5, interval counting is stopped and the VFP indicators are halted to mark the end of a VFP.

According to an embodiment of the present invention, a method is provided for predicting an episode of VTA by detection and analysis of various ventricular tachyarrhythmia prediction patterns (VTAPP). According to an embodiment of the present invention, a method is provided for predicting an episode of VTA by detection and analysis of multiple patterns of vagal fatigue during a predefined period of time. According to an embodiment of the present invention, a method is provided for predicting an episode of VTA by detection and analysis of the peak heart rate during one or more VFPs. In an embodiment, the identification of multiple patterns of vagal fatigue and/or the presence of a peak heart rate in excess of a defined threshold and/or duration may be used to predict an episode of VTA. For the purposes of embodiments of the present invention, the term "predefined period of time" refers to an amount of time, such as 1 hour, 2 hours, as opposed to a specific segment, such as 2:00-4:00 pm, even though the amount of time may overlap or match with a particular segment.

Methods in accordance with embodiments of the present invention may also be implemented using hardware, and thus may provide monitoring, prediction, and/or prevention capabilities. Embodiments of the present invention may include fully or partially implantable and/or external devices. Further, embodiments of the present invention may provide for notification of an imminent VTA.

Figure 1:
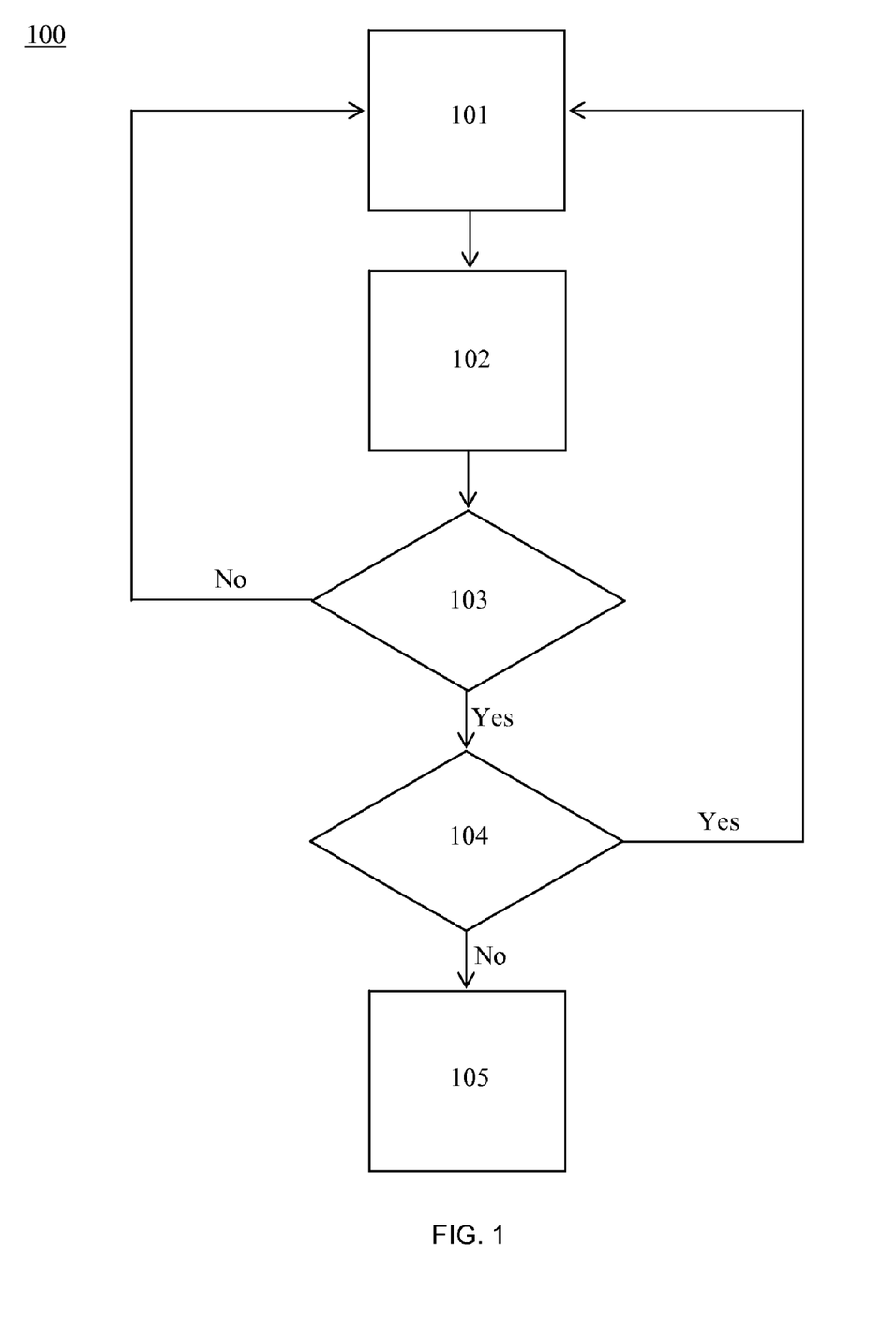
FIG. 1 is a flowchart showing an exemplary method in accordance with an embodiment of the present invention.

FIG. 1 is a flowchart showing an exemplary method 100 in accordance with an embodiment of the present invention. In block 101, a subject's heart is monitored with a suitable monitoring device (implantable device, ICD, pacemaker, electrode(s), external and/or internal cardiac monitors, electrocardiogram monitor, pulse oximeter with heart rate measurement, etc.), to collect data associated with the subject's heart. The collected data is then processed in block 102 to generate a number of metrics, for example, the R-R interval, heart rate or P-P interval. The metrics are further analyzed to determine whether a VFP exists. At diamond 103, a determination is made whether the analysis suggests that a VFP exists. If a VFP does not exist, the associated devices may continue to monitor the heart without initiating further action. In an embodiment of the present invention, the monitoring devices may continuously monitor the status of the heart independent of any analysis, processing or other action. In an embodiment, if a VFP does exist, a second determination is made at diamond 104. At diamond 104, a determination is made whether a predefined amount of time has expired since the previous occurrence of a VFP was detected. If a predefined amount of time has expired, the associated devices may continue to monitor the heart without initiating further action. If a predefined amount of time has not expired, a multiple-VFP condition exists and further action may be initiated at block 105. Such further action may include providing a warning or notification of a multiple-VFP condition and/or initiating action such as preventive pacing therapy to attempt to prevent a VTA from occurring. In an embodiment of the present invention, prior to initiating action, the method may optionally first provide for a determination of the current status of the heart to determine whether the heart is currently experiencing a VTA. In such a situation, preventive therapy would typically not be useful, and thus may be avoided.

A multiple-VFP condition refers to the occurrence of more than one VFP within a predefined period of time. In embodiments of the present invention, a method may be used to detect a minimum of 2, 3, 4, or more VFPs during a defined period of time to identify an imminent VTA. The period of time may be defined by a user based on the particular subject/patient, historical and/or statistical data. According to embodiments of the present invention, a suitable predefined period time in which the occurrence of multiple-VFPs may be used to indicate a condition of concern may be, for example, less than 5 hours, less than 3 hours, less than 2 hours, less than 1 hour, less than 30 minutes, etc. In an embodiment, a predefined period of time may be approximately 1.8 hours.

Embodiments of the present invention provide prediction of VTAs with a sensitivity of at least approximately 45%, for example at least approximately 50%, such as at least approximately 55%, a specificity of at least approximately 80%, for example at least approximately 90%, such as at least approximately 95%, and a type II error rate of less than approximately 3 events per day, such as less than approximately 1 event per day. For the purposes of various embodiments of the present invention, the term sensitivity refers to the percentage of accurately identified episodes of VTA based on detection of one or more VFP. For the purpose of various embodiments of the present invention, the term specificity refers to the percentage of periods of time, without VTA, of duration comparable to those used to determine sensitivity, that are correctly classified by the method as without VFP. For the purposes of various embodiments of the present invention, the term type II error rate refers to the rate of VFPs detected, whether single or multiple, that are not followed by a VTA during the specified time period. For the purposes of various embodiments of the present invention, the term R-R interval refers to the duration between two consecutive R waves of an electrocardiogram.

In an embodiment, sensitivity and specificity may be adjusted by utilizing the duration of the VFP as the sole or contributing factor for predicting an episode of VTA. In an embodiment, to qualify as a component of VTA prediction, the VFP must last for at least an established duration, such as 40 R-R intervals (~30 seconds), 50 R-R intervals, or 65 R-R intervals, or at least 30, 35, 40, 45, 50, 55, 60, or more seconds. In embodiments, an exemplary number of VFPs may be 2 or more during a time interval of approximately 1.8 hours.

In an embodiment, a threshold heart rate may be established, above which concern may be raised and/or a prediction may be made as to an imminent VTA. Sensitivity and specificity of VTA prediction may be further controlled by utilizing the peak heart component in addition with identification of single or multiple VFPs. In embodiments, exemplary threshold heart rates that may be established and utilized as described above may be 82, 84, 86, 88, 90, or more bpm.

In an embodiment in which a peak heart rate is used in combination with multiple episodes of VFP during a defined period of time to predict an episode of VTA, the threshold-exceeding heart rate must be above the threshold for at least an established duration and/or, in an embodiment, must occur during at least one of the episodes of VFP to signal an imminent VTA. In an embodiment, to qualify as a component of VTA prediction, the mere occurrence of a peak heart in excess of a threshold may be utilized, and/or in an embodiment, a heart rate above a threshold for a period of time, such as at least 10, 20, 30, 40, or more seconds, may be utilized.

Figure 2:
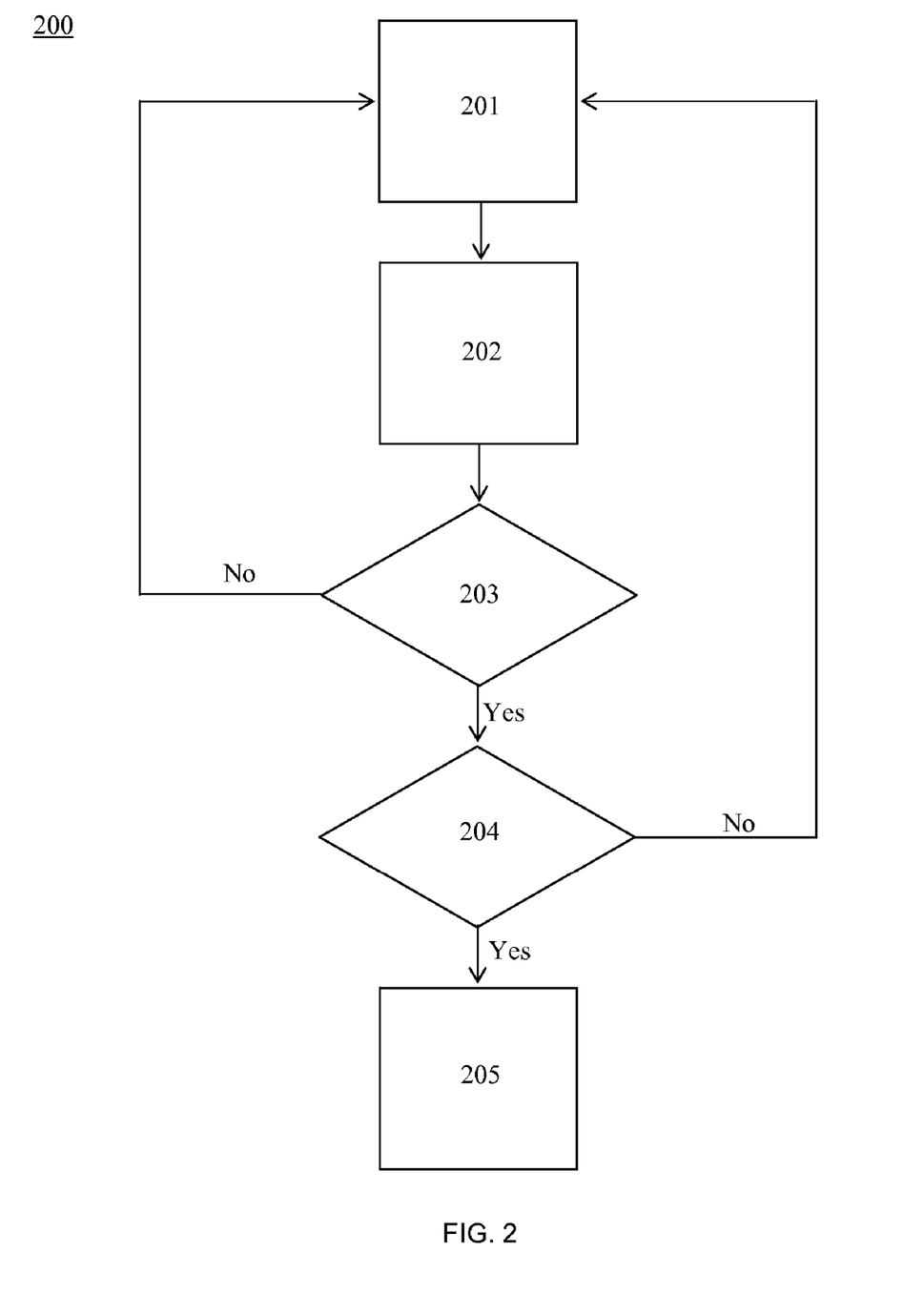
FIG. 2 is a flowchart showing an exemplary method in accordance with an embodiment of the present invention.

FIG. 2 is a flowchart showing an exemplary method 200 in accordance with an embodiment of the present invention. In block 201, a subject's heart is monitored with a suitable monitoring device (implantable device, ICD, pacemaker, electrode(s), external and/or internal cardiac monitors, electrocardiogram monitor, pulse oximeter with heart rate measurement, etc.), to collect data associated with the subject's heart. The collected data is then processed in block 202 to generate a number of metrics, for example, the R-R interval, heart rate or P-P interval. The metrics are further analyzed to determine whether a peak heart rate in excess of an established threshold exists. At diamond 203, a determination is made whether a VFP with sufficient duration has been detected and, if programmed, whether a multiplicity of such patterns has been detected within a preprogrammed time duration. If such a single pattern or multiplicity of VFPs has not been detected, the associated devices may continue to monitor the heart without initiating further action. In an embodiment of the present invention, the monitoring devices may continuously monitor the status of the heart independent of any analysis, processing or other action. In an embodiment, if a single pattern or multiplicity of VFPs does exist, a second determination is made at diamond 204. At diamond 204, a determination is made whether the heart rate has been above the established threshold at any time during at least one of the VFPs. If the heart rate was not above the established threshold, the associated devices may continue to monitor the heart without initiating further action. If the heart rate was above the established threshold during a VFP, a condition exists that may suggest the imminent occurrence of a VTA and further action may be initiated at block 205. Such further action may include providing a warning or notification of the heart rate status and/or initiating action such as preventive pacing therapy to attempt to prevent a VTA from occurring. In an embodiment of the present invention, prior to initiating action, the method may optionally first provide for a determination of the current status of the heart to determine whether the heart is currently experiencing a VTA. In such a situation, preventive therapy would typically not be useful, and thus may be avoided.

Figure 3:
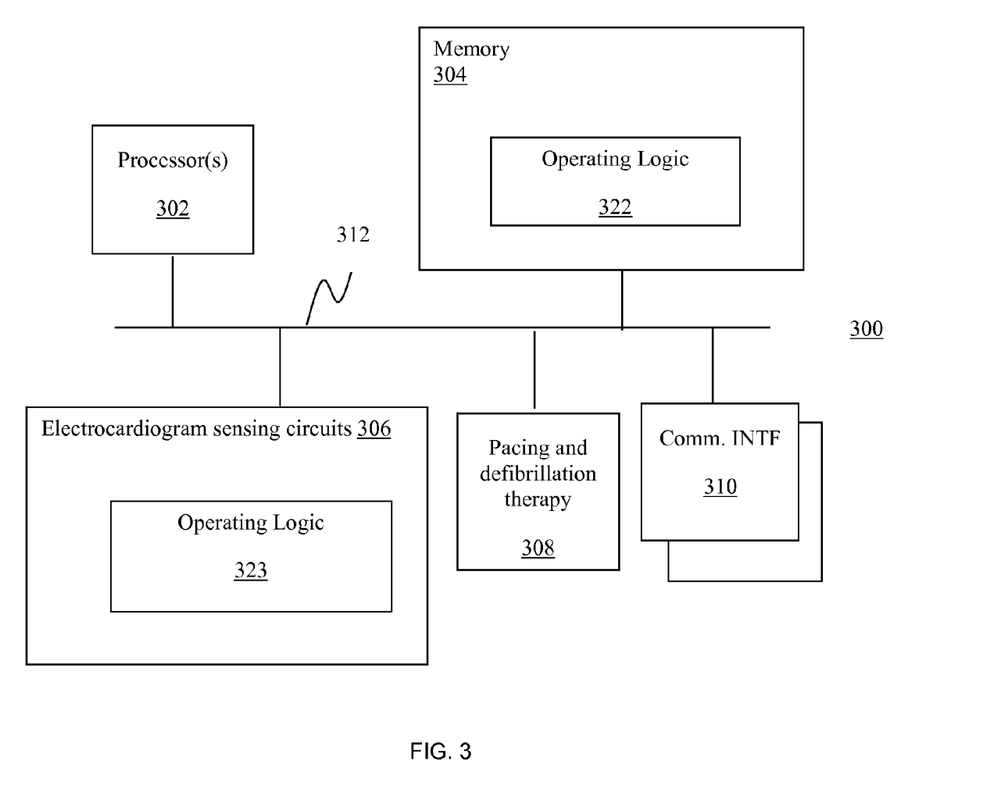
FIG. 3 illustrates an exemplary computing device suitable for use in accordance with various embodiments of the present invention.

FIG. 3 illustrates a block diagram view of an exemplary computing device suitable for use in one or more of the embodiments of the present invention. As illustrated, computing device 300 includes processor 302, memory 304 coupled to each other via bus 312. Further, computing device 300 also includes electrocardiogram sensing circuits 306 with operating logic 323, pacing and defibrillation therapy 308, and communication interface 310 coupled to the earlier described elements as shown.

Each of the elements represents a broad range of the corresponding element known in the art or to be designed consistent with the teachings of the embodiments of the present invention. They perform their conventional functions, i.e. processing, storage, and so forth. In particular, memory 304 may be employed to store temporal and persistent copies of operating logic 322, which may be adapted to practice all or selected aspects of the various methods of the various embodiments of the present invention.

In various embodiments of the present invention, communication interface 310 may include mechanisms for communication from inside the body to an external device, as is known in the art, such as pacemakers and ICDs. In various embodiments of the present invention, computing device 300 may be an ICD or pacemaker, which may be linked to an external desktop computer, a tablet computer or a palm sized computing device through communication interface 310. The external link may be occasional, for example during follow-up, or continual, for example through a radio-frequency or electro-magnetic coupling link. In various embodiments of the present invention, device 300 may be an external monitoring system, with conventional surface electrocardiogram circuit 306, which may be interfaced to a pacing and defibrillation device 308 and which communicates with a hospital network through Communication Interface 310.

Embodiments of the present invention provide methods for predicting VTA as well as preventing episodes of VTA from occurring. Embodiments of the present invention may be incorporated into or combined with preventive therapies and devices, such as a pacemaker, ICD, external defibrillator, and/or various anti-arrhythmic drugs to provide systems for predicting and preventing VTA.

EXAMPLES

Example I

Analysis of VFP Episodes as VTA Predictor

The following R-R histories (A, B and C) were analyzed for VFP: A) Twenty-three 24-hour Holter records from one set of subjects referred to as the VA-ICD data set. Each subject had ICD implanted prior to beginning the study. Each subject wore a Holter monitor for 24 hours. No episode of VTA was detected during Holter monitoring. B) 208 records from Biotronik ICDs. The average record length was about 1.6 hours prior to an episode of VTA. This is referred to as the Bio-ICD data set. This data set does not include records during which the subject was either bradycardic or had an episode of atrial tachyarrhythmia. C) Seven 24-hour Holter records of normal subjects from the MIT-BIH "long term" data base. This is referred to as the MIT-BIH data set.

In this example set, all VFP signs/episodes that occur within a sliding window of 65 R-R intervals long (~40 s) are considered to be part of one episode. While a number of parameters may be used to optimize the performance of a VFP-based VTA prediction algorithm, the duration threshold is used in this example set.

Using the VA-ICD data set, random records may be created that match the Bio-ICD data set in record length. For each of these surrogate-VA-ICD records, a random VA-ICD record and a random starting point may be selected. If VTA episodes are independent of VFP episodes, then one may expect to have about the same number of records exhibiting VFP episodes in both the Bio-ICD and the surrogate-VA-ICD data sets. The results of this exemplary study are summarized in Table I.

TABLE I

Incidence of vagal fatigue in the actual Bio-ICD data set and record length matching surrogate-VA-ICD data set.

| Duration Threshold | Bio-ICD | Surrogate-VA-ICD |
|---|---|---|
| 65 | 42.3% | 6.5% |
| 50 | 61.1% | 17.7% |

Statistically, with $p<<0.05$, the two distributions are different. Thus, it appears that episodes of VFP are associated more frequently (~6.5× in this example) with episodes of VTA in the ICD population.

Figure 4:
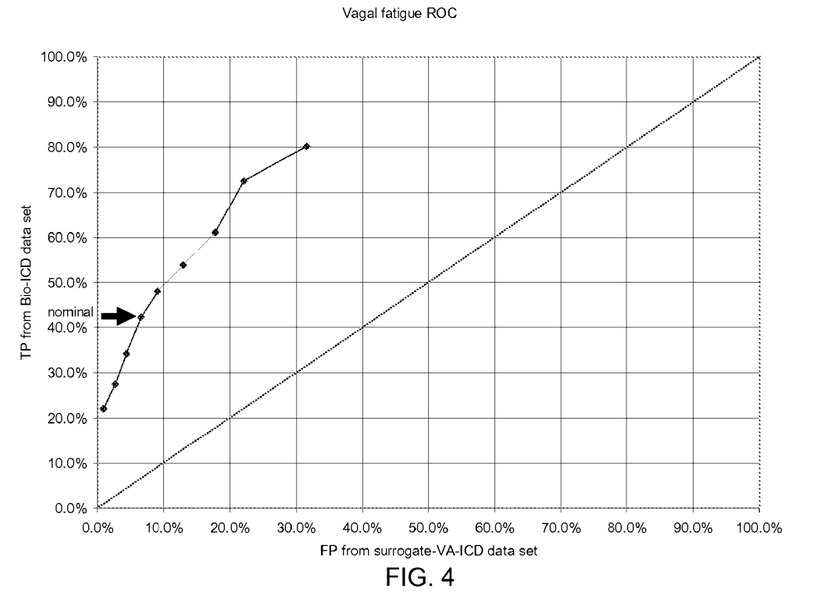
FIG. 4 shows a receiver operating curve (ROC) of vagal fatigue prediction of a ventricular tachyarrhythmia (VTA) based on Bio-ICD and surrogate-VA-ICD data sets in accordance with an embodiment of the present invention.

While the records in the surrogate-VA-ICD data set may not be strictly independent, one may assume that the original VA-ICD data set is representative of ICD wearers during non-VTA periods, and thus the surrogate-VA-ICD data set may be considered a record-matched data set from which one may determine the approximate specificity of the VFP indicator. By varying the duration threshold value, one may arrive at the receiver operating curve (ROC) shown in FIG. 4.

Figure 5:
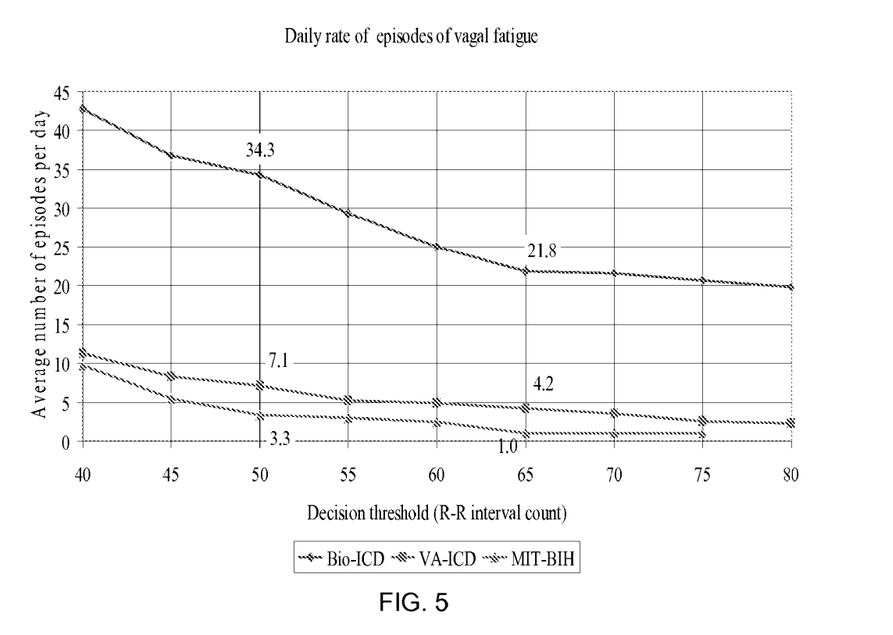
FIG. 5 is a graph plotting daily rate of vagal fatigue episodes as a function of duration threshold in accordance with an embodiment of the present invention.

At the duration threshold of 65 R-R intervals, the sensitivity is approximately 40-45% (42.3% from Table I), and the specificity is 93.5% (6.5% false positive from Table I). In embodiments of the present invention, a more meaningful measure than the specificity may be the daily (24 hour) rate of VFP in the VA-ICD population, which is effectively the type II error rate, with the assumption that the VA-ICD data set is representative of the non-VTA condition. This is shown in FIG. 5. At the duration threshold of 65 R-R intervals, the type II error rate based on the VA-ICD data set is only 4.2 events/day in the subjects with VFP and 1.8 events/day in the overall population.

Methods in accordance with embodiments of the present invention may provide increased sensitivity and/or a decreased rate of type II error. One way to increase sensitivity may be to decrease the duration threshold. For example, going from 65 R-R intervals to 50 R-R intervals, the sensitivity as shown in Table 1 may increase from 42.3% to 61.1%. From Table I, going from 65 R-R intervals to 50 R-R intervals, the specificity decreases from 93.5% to 82.3%. The rate of type II error, as shown in FIG. 5, increases from 4.2 events/day to 7.1 events/day in subjects with episodes of VFP.

If, in addition to reducing the duration threshold, a rate of VFP corresponding to multiple events over a defined period of time is used as part of the VTA prediction method, the type II error rate may be decreased with a corresponding increase in specificity.

For example, according to an embodiment of the present invention, a rate of VFP corresponding to 2 events in a period of less than 2 hours, for example 1.8 hours, may provide a reduction in the type II error rate as described in this example set.

Figure 6:
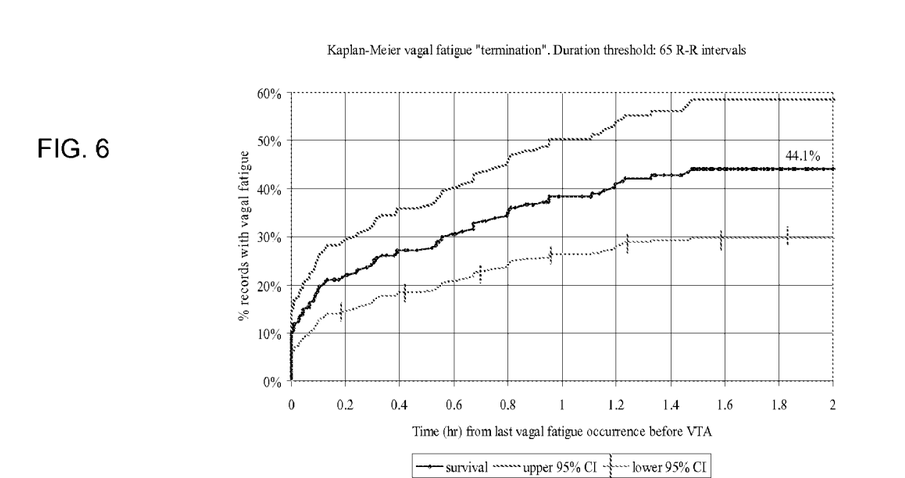
FIG. 6 shows a Kaplan-Meier termination curve for vagal fatigue prior to ventricular tachyarrhythmia (VTA) in accordance with an embodiment of the present invention.
Figure 7:
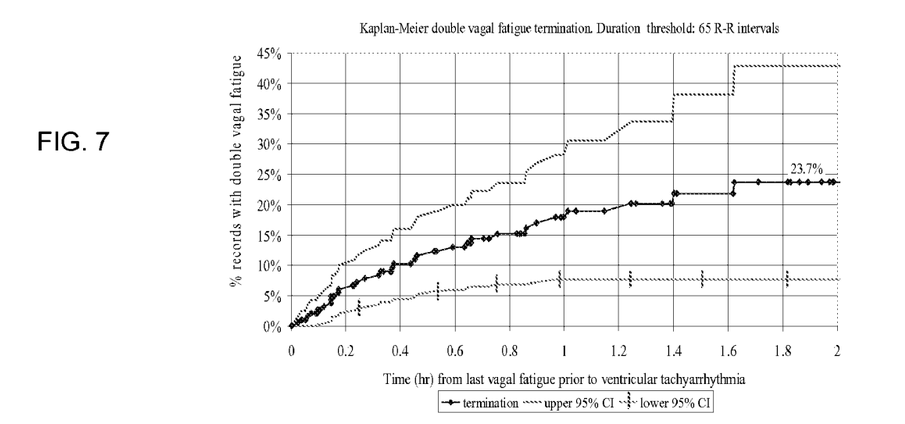
FIG. 7 shows a Kaplan-Meier curve for double vagal fatigue for a duration threshold of 65 R-R intervals in accordance with an embodiment of the present invention.

Considering the Bio-ICD records, at a duration threshold of 65 R-R intervals, with at least one VFP within 1.8 hours from the VTA, one may derive a Kaplan-Meier termination curve for the prior VFP event. This is shown in FIG. 6. A total of 44.1% of the records have a VFP within 1.8 hour from the VTA. Next consider those Bio-ICD records, with at least two VFPs prior to the VTA. The Kaplan-Meier termination curve for those with two prior VFPs within the indicated time is shown in FIG. 7. Thus, the double VFP sensitivity for this example set is 23.7%. The double VFP specificity in this example set was found to be ~100% (no double VFP in the surrogate-VA-ICD data set). The type II error rate reduces to (10 events in VA-ICD data set) 0.44 event/day.

Figure 8:
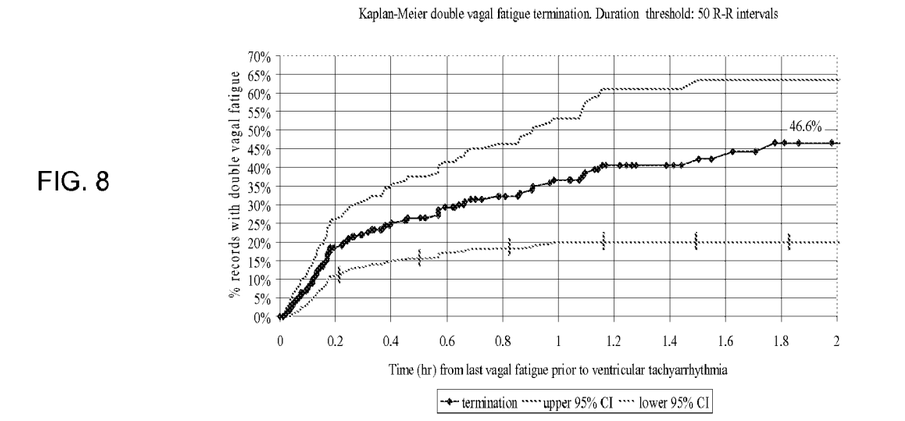
FIG. 8 shows a Kaplan-Meier termination curve for double vagal fatigue prior to ventricular tachyarrhythmia (VTA) for a duration threshold of 50 R-R intervals in accordance with an embodiment of the present invention.

Reducing the duration threshold to, for example, 50 R-R intervals, the corresponding double VFP sensitivity becomes 46.6% in this example set, as shown in FIG. 8. The double VFP specificity is found to be 95.2% (10 false positives/208 records in the surrogate-VA-ICD data set). The type II error rate (16 double VFP episodes in the VA-ICD data set) becomes 0.7 event/day.

Thus, in the present example set, using an observation time of 1.8 hour, a sensitivity of 47% for predicting an imminent episode of VTA may be achieved with a type II error rate of only 0.7 event/day (and associated specificity of 95%), using a double vagal fatigue method in accordance with an embodiment of the present invention. In this example set, a VTA may be expected within 1.8 hour from the double vagal fatigue event.

Example II

Combination of VFP Episodes and Peak Heart Rate

In accordance with an embodiment, the Bio-ICD data set was analyzed and a combination of criteria were used, namely two VFPs need to occur within a period of 1.8 hours and the heart rate during these accelerations exceeds 86 bpm (700 ms) to provide a positive prediction of VTA. The specificity was tested using R-R records matched in duration from 26 control patients with defibrillators during normal periods. R-R records used in this example were selected according to the following criteria: at least 600 R-R intervals long, no visible indication of pacing in the record, and no visible indication of supraventricular tachyarrhythmia in the record.

The basic acceleration pattern was expected to be found during sinus rhythm in the 1.8 hour period prior to 83% of episodes of ventricular tachyarrhythmia. It was also found in 43% of the matched set of non-arrhythmic records, corresponding to a specificity of 57%. With the requirement of VFP multiplicity within 1.8 hours and peak heart rate exceeding 86 bpm, the sensitivity of the proposed predictor is reduced to 53%, but the specificity is increased to 91%, which corresponds to an average false positive rate of 0.8 event/day across the patient population. Thus, in an embodiment, a VTA predictor based on a pattern of heart rate acceleration is provided that yields sensitivity from 53% to 83%, with specificity up to 91%. Instances of such a VTA predictor increase significantly prior to an episode of tachyarrhythmia.

Figure 9:
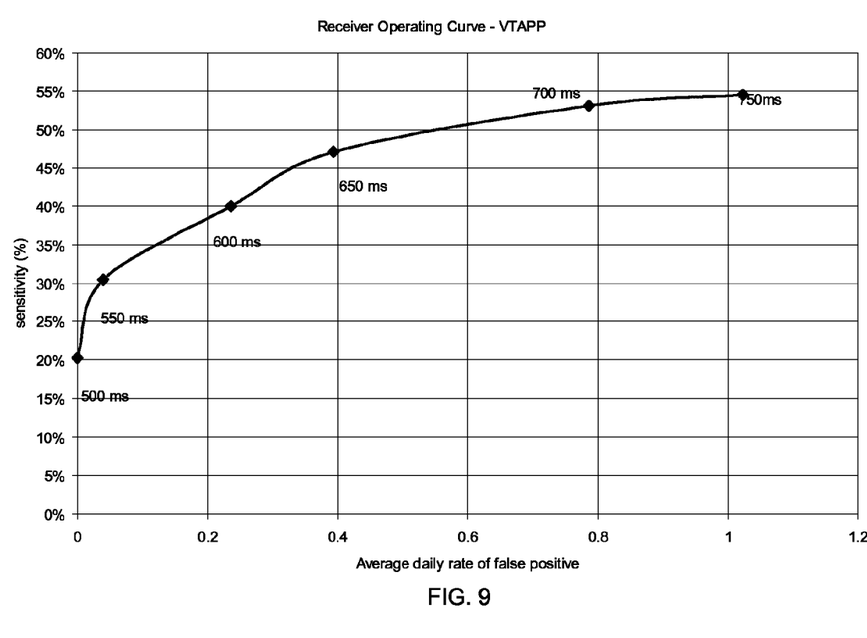
FIG. 9 shows a receiver operating curve for a ventricular tachyarrhythmia prediction pattern (VTAPP) in accordance with an embodiment of the present invention.

In an embodiment, the peak heart rate may be used to fine-tune the prediction pattern by trading off sensitivity for false alarm rate, as shown by the receiver operating curve of FIG. 9. In FIG. 9, the parameter being varied is the minimum R-R interval detected during the rhythm acceleration patterns.

Figure 10:
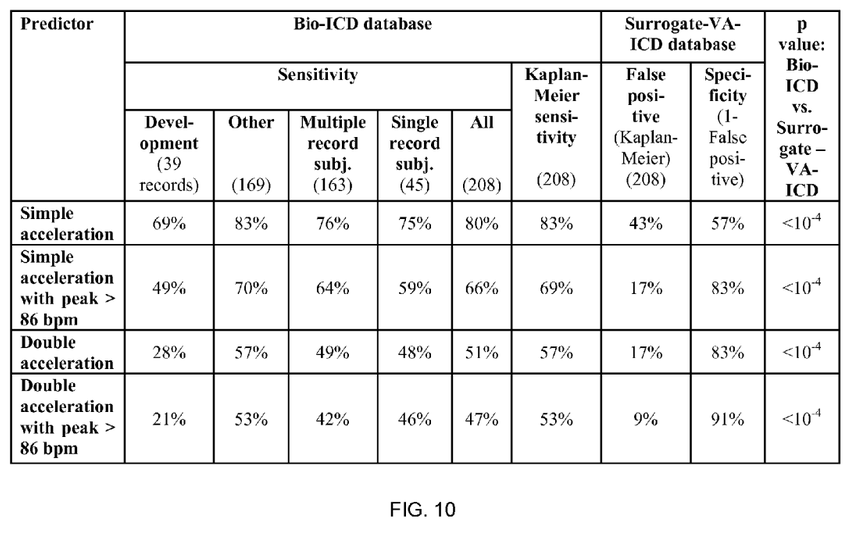
FIG. 10 shows a table illustrating sensitivity and specificity values for various data sets for various VTA prediction patterns and factors considered in accordance with an embodiment of the present invention.
Figure 11:
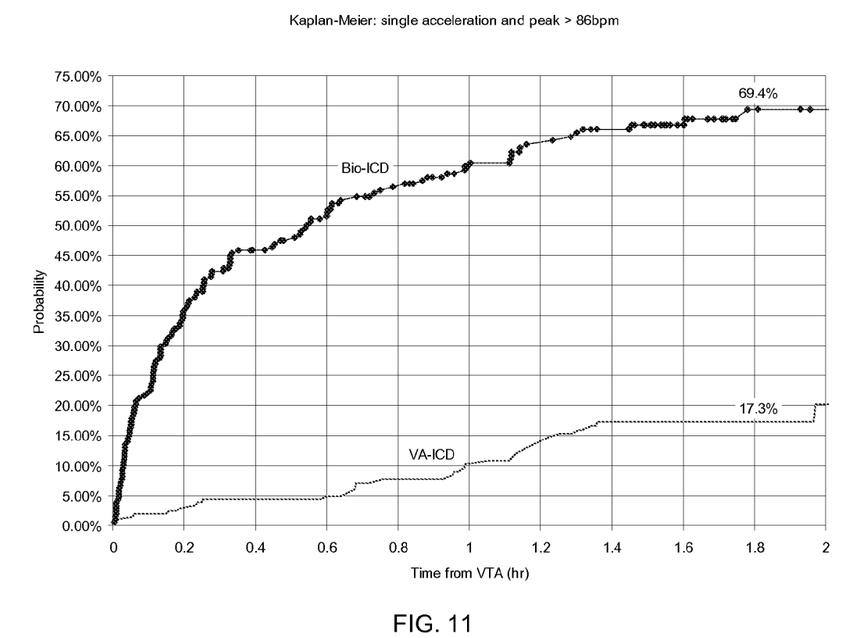
FIG. 11 shows Kaplan-Meier curves for a single/simple acceleration pattern with a peak heart rate greater than 86 bpm in accordance with an embodiment of the present invention.
Figure 12:
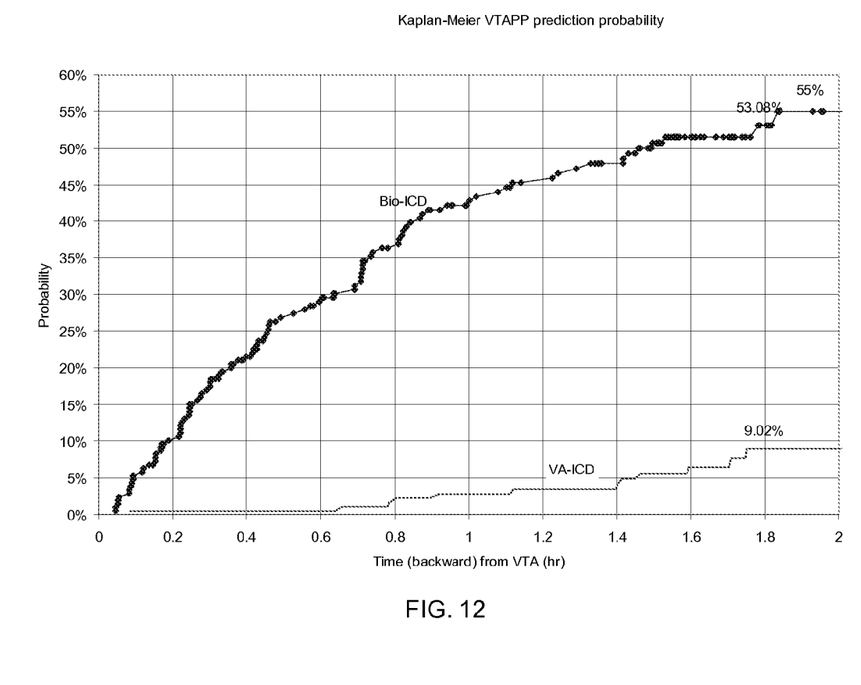
FIG. 12 shows Kaplan-Meier curves for prediction probability using a combination of a double acceleration occurrence and a peak heart rate above 86 bpm in accordance with an embodiment of the present invention.

FIG. 10 provides a table illustrating sensitivity and specificity values for various data sets discussed above for various patterns and factors considered. The Kaplan-Meier curves for a single/simple acceleration pattern with a peak heart rate greater than 86 bpm are shown in FIG. 11. The Kaplan-Meier curves for prediction probability using a combination of a double acceleration occurrence and a peak heart rate above 86 bpm are shown in FIG. 12.

Figure 13:
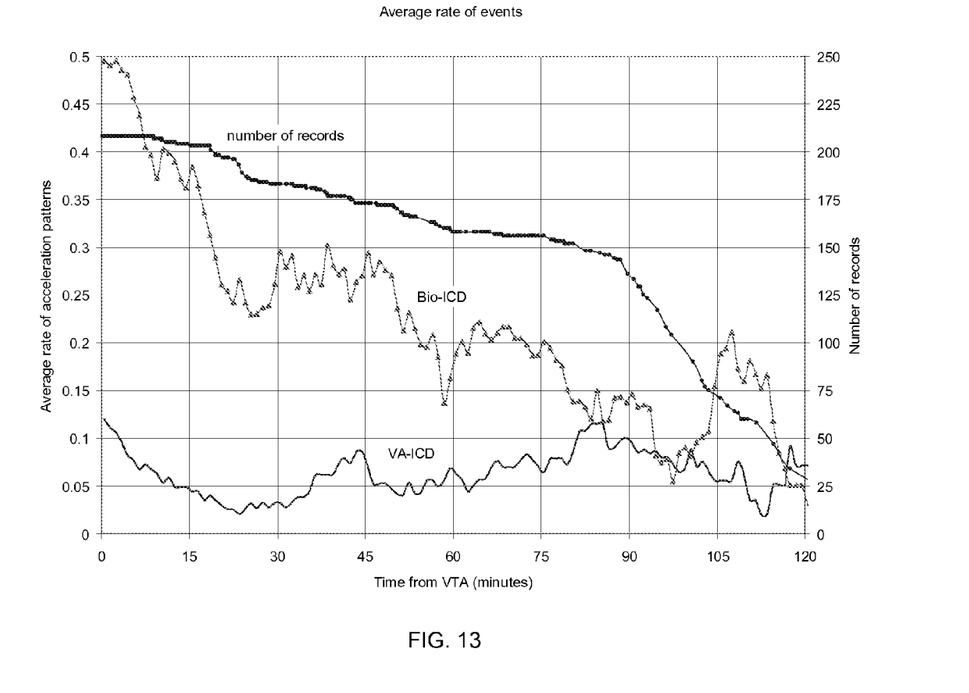
FIG. 13 illustrates the average rate of acceleration patterns in accordance with an embodiment of the present invention.

FIG. 13 illustrates the average rate of acceleration patterns in accordance with an embodiment of the present invention. FIG. 13 shows that monotonic accelerations are more likely to occur just prior to episodes of VTA than earlier in the monitoring period, and at a higher rate than in random records of ICD patients. FIG. 13 shows 10 minute sliding averages, along with the curve showing the number of active records. If there is a link between VTA and the acceleration pattern(s), one would expect that as the VTA becomes more imminent, there would be an increase in the rate of acceleration patterns. This is confirmed in FIG. 13 in which it may be seen that the majority of episodes of monotonic acceleration occur in the 20 minutes prior to an episode of VTA. The higher frequency of these accelerations in patients prior to an episode of VTA compared to that seen in the control population and the clustering of the accelerations in the few minutes before an episode of VTA suggest these accelerations may be caused by a change in the autonomic regulation which is also responsible for the VTA.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method for predicting an occurrence of ventricular tachyarrhythmia in a subject, comprising:
   detecting for a first pattern of vagal fatigue exhibited by the subject;
   detecting for at least one additional pattern of vagal fatigue exhibited by the subject prior to expiration of a period of time after detecting said first pattern of vagal fatigue; and
   detecting for a heart rate in excess of an established threshold during at least one vagal fatigue pattern, wherein the detections of said first pattern and said at least one additional pattern of vagal fatigue within said period of time and the detection of said heart rate in excess of an established threshold are performed to facilitate prediction of an occurrence of ventricular tachyarrhythmia in said subject.

2. The method of claim 1, wherein the method further comprises selecting said period of time to be less than 3 hours.

3. The method of claim 1, wherein the method further comprises selecting said period of time to be less than 2 hours.

4. The method of claim 1, wherein said detections are performed to facilitate prediction of an imminent occurrence of ventricular tachyarrhythmia.

5. The method of claim 1, wherein said detections are performed to facilitate prediction of an occurrence of ventricular tachyarrhythmia predicted to occur in less than 3 hours.

6. The method of claim 1, wherein said detections are performed to facilitate prediction of an occurrence of ventricular tachyarrhythmia predicted to occur in less than 2 hours.

7. The method of claim 1, wherein said detections are performed to facilitate prediction of an occurrence of ventricular tachyarrhythmia predicted to occur in less than 30 seconds.

8. The method of claim 1, wherein said established threshold is at least 86 bpm.

9. A method for preventing an occurrence of ventricular tachyarrhythmia in a subject, comprising:
   predicting for an occurrence of ventricular tachyarrhythmia in said subject based at least in part on one or more detected vagal fatigue patterns and a heart rate exceeding an established threshold by the subject during at least one of said one or more vagal fatigue patterns; and
   initiating at least one preventive action to prevent said predicted occurrence of ventricular tachyarrhythmia from occurring.

10. The method of claim 9, wherein said initiating of a preventive action comprises providing a warning or notification of said predicted occurrence of ventricular tachyarrhythmia.

11. The method of claim 9, wherein said initiating of a preventive action comprises initiating a preventive cardiac pacing therapy.

12. The method of claim 9, wherein said initiating of a preventive action comprises providing at least one anti-arrhythmic drug to said subject.

13. The method of claim 9, wherein the method further comprises determining whether said subject is experiencing a ventricular tachyarrhythmia, prior to said initiating of a preventive action.

14. An apparatus comprising:
   a cardiac monitor configured to detect vagal fatigue patterns and a heart rate exhibited by a subject during said vagal fatigue patterns; and
   a processor coupled to the cardiac monitor and programmed to receive from said cardiac monitor data indicative of detected vagal fatigue patterns and a heart rate in excess of an established threshold, and to predict an occurrence of ventricular tachyarrhythmia in the subject, based at least in part on the received data.

15. The apparatus of claim 14, wherein said cardiac monitor comprises an implantable cardioverter defibrillator, a pacemaker, or an external cardiac monitor.

16. The apparatus of claim 14, wherein the apparatus further comprises a device coupled to the processor and configurable to be controlled by the processor to take a preventive action to prevent a predicted occurrence of ventricular tachyarrhythmia in the subject from occurring.

17. The apparatus of claim 16, wherein said device comprises an implantable cardioverter defibrillator or an implantable drug delivery device.

18. An apparatus comprising:
   a processor adapted to receive data indicative of detected vagal fatigue patterns and a heart rate in excess of an established threshold exhibited during said vagal fatigue patterns, and to predict an occurrence of ventricular tachyarrhythmia in the subject, based at least in part on the received data; and a device coupled to the processor and configurable to be controlled by the processor to take a preventive action to prevent a predicted occurrence of ventricular tachyarrhythmia in the subject from occurring.

19. The apparatus of claim 18, wherein said device comprises an implantable cardioverter defibrillator or an implantable drug delivery device.

* * * * *